US00PP27989P2

(12) United States Plant Patent
Hansen

(10) Patent No.: US PP27,989 P2
(45) Date of Patent: May 9, 2017

(54) ***DIANTHUS* PLANT NAMED 'SWEETIE PIE'**

(50) Latin Name: ***Dianthus* hybrid**
Varietal Denomination: Sweetie Pie

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 14/998,556

(22) Filed: Jan. 19, 2016

(51) Int. Cl.
*A01H 5/02* (2006.01)

(52) U.S. Cl.
USPC ..... Plt./276

(58) Field of Classification Search
USPC ..... Plt./276, 277, 281, 282
CPC ..... A01H 5/0233
See application file for complete search history.

*Primary Examiner* — Kent L Bell

(57) ABSTRACT

A new and unique plant cultivar of perennial carnation or pinks, *Dianthus* plant named 'Sweetie Pie' with numerous, fully-double, fragrant flowers, on branched stems having up to 4 flowers per stem. Petals are pink that lighten with age. Plant has vigorous compact habit with silvery gray-green foliage. *Dianthus* 'Sweetie Pie' is tolerant of high temperatures and resists center die-out. *Dianthus* 'Sweetie Pie' flowers in late spring and again in early fall.

1 Drawing Sheet

Botanical denomination: *Dianthus* hybrid.
Cultivar designation: 'Sweetie Pie'.

BACKGROUND OF THE INVENTION

The present invention relates to the new and distinct cultivar of carnation or pinks from the genus *Dianthus* and given the cultivar name 'Sweetie Pie' previously known only internally by the breeder code 11-283-01. The new plant was the result of an intentional cross on May 24, 2011 by the inventor between *Dianthus* 'Devon Flavia' U.S. Plant Pat. No. 15,903 as the female or seed parent and 'Pomegranate Kiss' U.S. Plant Pat. No. 21,895 as the male or pollen parent. Seeds of the cross were harvested Jul. 13, 2011. The new hybrid was fast isolated from trials at a wholesale perennial nursery in Zeeland, Mich. during the summer of 2012 as a single seedling plant and given the breeder number 11-283-01 during the remaining evaluation processes. *Dianthus* 'Sweetie Pie' has been asexually propagated at the same nursery in Zeeland, Mich. since 2012 using traditional shoot tip cutting procedures and found to reproduce plants that are identical and exhibit all the characteristics of the original plant.

No plants of *Dianthus* 'Sweetie Pie' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventor.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant.

Comparing the new plant with the female parent, 'Devon Flavia', the new plant has a deeper pink flower petal color. Compared to the male parent, 'Pomegranate Kiss', the new plant has lighter pink flowers rather than the burgundy flowers of 'Pomegranate Kiss'. Other similar *Dianthus* include: 'Devon PP 11' U.S. Plant Pat. No. 14,919; 'Devon Siskin' U.S. Plant Pat. No. 14,377; 'Devon Winnie' U.S. Plant Pat. No. 14,893; 'Dragon Fruit' U.S. Plant Pat. No. 21,894, 'Noreen' U.S. Plant Pat. No. 20,369; 'Starlette' U.S. Plant Pat. No. 21,438 and 'WP10 XAV04' U.S. Plant Pat. No. 24,018.

Table 1 below shows further comparisons.

Table 1

| CULTIVAR | Leaf color | Flower color | Size (H × W) |
|---|---|---|---|
| 'Devon PP 11' | gray-green | pink | 25 cm × 30 cm |
| 'Devon Flavia' | medium green | sugar pink | 30 cm × 15 cm |
| 'Devon Siskin' | blue-green | light pink | 25 cm × 20 cm |
| 'Devon Winnie' | blue-green | dark pink | 20 cm × 15 cm |
| 'Dragon Fruit' | gray-green | fuchsia pink | 20 cm × 30 cm |
| 'Noreen' | gray-green | raspberry-pink | 15 cm × 15 cm |
| 'Starlette' | gray-green | raspberry-pink | 18 cm × 17 cm |
| 'Sweetie Pie' | silvery blue-green | pink | 25 cm × 26 cm |
| 'WP10 XAV04' | silver gray | bubblegum pink | 28 cm × 12 cm |

| CULTIVAR | # Petals | Ground petal color | Petal band/mark |
|---|---|---|---|
| 'Devon PP 11' | 15-20 | N74C, 75B | none |
| 'Devon Flavia' | 25-40 | 62B | reddish-purple |
| 'Devon Siskin' | 5 | 74D-69D | magenta edge |
| 'Devon Winnie' | 7-35 | N66D | none |
| 'Dragon Fruit' | 14-22 | N74A-N74B | reddish-purple |
| 'Noreen' | 5 | 72C | none |
| 'Starlette' | 15-20 | 70B | none |
| 'Sweetie Pie' | 16-20 | 71D | none |
| 'WP10 XAV04' | 35-40 | 62A | none |

*Dianthus* 'Sweetie Pie' is distinct from its parents and all other *Dianthus* known to the applicant in the following combined traits:

1. Fully-double flowers with numerous overlapping pink petals.
2. Petals having a serrate to crenate apex.
3. Numerous, compact branched stems with multiple flowers per stem.
4. Large flower size producing a lightly sweetly clove-like fragrance.
5. High heat tolerance with no vernalization required for flower production.
6. Floriferous, vigorous, with densely compact habit and finely-textured silvery gray-green foliage.

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
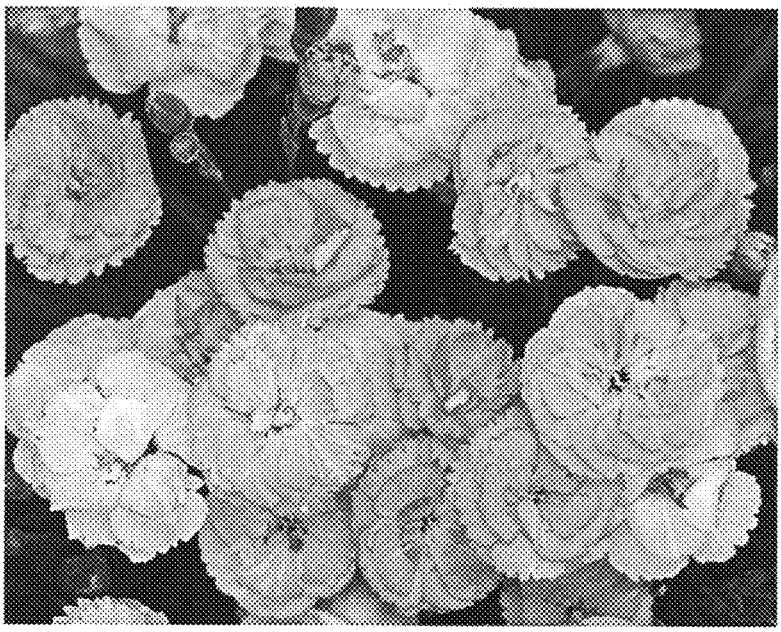
FIG. 1 s a close-up of the buds and flowers with young and old flower colors.
Figure 2:
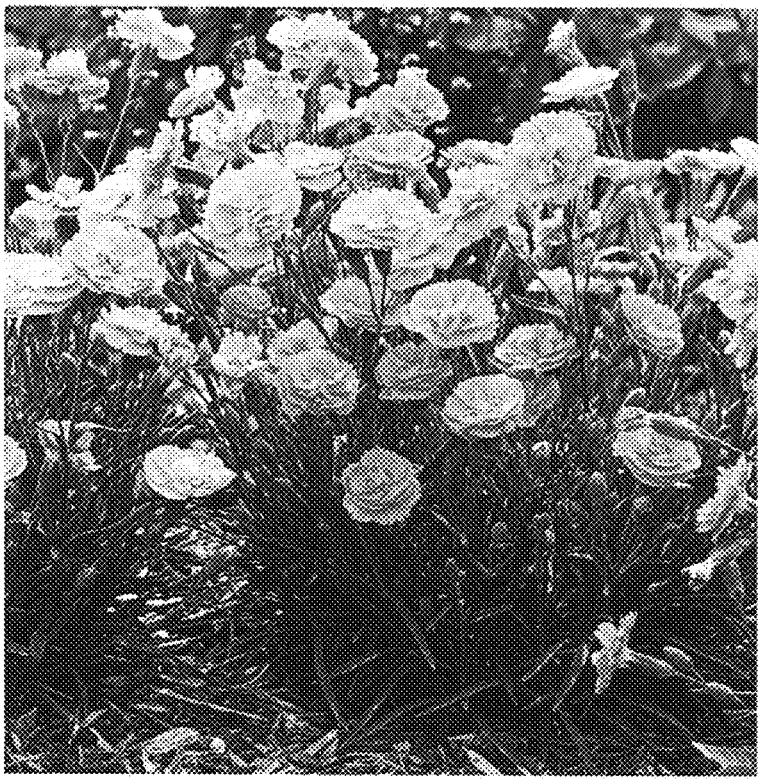
FIG. 2 shows the habit of a greenhouse-grown, one-year old plant in mid-season flowering.

The following detailed description of the new plant is based on observations of one-year old plants in greenhouse-grown containers at a nursery in Zeeland, Mich. with light shade, supplemental watering, light additions of fertilizer and free of other plant growth regulators. All color usage is in accordance with the 2001 edition of The Royal Horticultural Colour Chart except where common dictionary terms are used.

Botanical classification: *Dianthus* hybrid.

Parentage: 'Devon Flavia' U.S. Plant Pat. No. 15,903 as the female or seed parent and 'Pomegranate Kiss' U.S. Plant Pat. No. 21,895 as the male or pollen parent.

Plant description:

*Habit*.—Caespitose, herbaceous, compact evergreen perennial; stems and peduncles branched, erect stems; height of foliage about 14.0 cm and about 27.0 cm across; height in flower is about 25.0 cm.

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, glaucous on adaxial and abaxial surfaces; margin entire; acute apex; base decurrent, adpressed along stem and slightly perfoliate; no fragrance detected.

*Leaf dimensions*.—To about 8.5 cm long and about 4.0 mm wide, average about 6.0 cm long and 3.0 mm wide.

*Leaf color*.—Young greenhouse-grown expanding leaves abaxial and adaxial nearest RHS 138A; mature adaxial nearest RHS 139A and abaxial between RHS N138A and RHS 137A; under full sun field conditions abaxial and adaxial surfaces between RHS 122B and RHS 122C.

*Venation*.—Not pronounced; obscurely pinnate, coloration same as that of leaf adaxial and abaxial surfaces.

Stems: Terete, glabrous, glaucous; erect to about 75 degrees from vertical; branching at alternate nodes; about 50 per plant.

*Stem size*.—About 17.0 cm long and about 3.0 mm wide at base.

*Stem color*.—Nearest RHS N138C.

*Branching*.—Numerous, concentrated in lower leaf axils; about 12 per main stem and about 600 per plant; branch size average about 5.0 cm long and about 3.0 mm diameter at base at time of initial flowering.

*Nodes*.—About 4.0 mm across; color nearest RHS 145D.

*Internodes*.—Average about 1.5 cm apart depending on growing temperature, shorter in basal nodes and in cooler conditions.

Inflorescence:

*Type*.—Terminal, cymose; salverform; actinomophic; completely double.

*Attitude*.—Upright to mostly upright.

*Dimension*.—About 4.3 cm across and extending about 15.0 mm above calyx.

*Flowers per stem*.—Typically two.

*Pedicel*.—Glaucous, glabrous, terete.

*Pedicel size*.—Terminal flower about 4.0 mm long and about 1.0 mm diameter; other flowers average about 20.0 mm long and 1.0 mm diameter.

*Pedicel color*.—Nearest RHS N138C with glaucous covering of nearest RHS 122C.

*Flower bud one day prior to opening*.—Glaucous, glabrous, ellipsoid with rounded apex and rounded base.

*Flower bud size*.—One day prior to opening — about 2.0 cm long and about 8.0 mm wide; while petals still enclosed in calyx — about 1.8 cm long and about 8.0 mm wide.

*Flower bud color*.—While still enclosed in calyx — between RHS 122C and RHS N138A at apex and nearest RHS N138D at base; with petals exposed and still tight — petals between RHS 64B and RHS 64C and calyx same as while petals still enclosed in calyx.

*Flower period*.—Beginning late spring and repealing in early fall; effective about four weeks per flowering season.

*Flower fragrance*.—Light, sweet spicy, clove-like.

*Flower lasting quality*.—About eight days on or cut from plant.

*Petals*.—Glabrous; 16 to 20 per flower; consisting of a rounded limb or blade and a claw, outer petals with broader and more rounded limb; limb and claw combined are obovate with long tapered claw; apex and margin with irregular dentations about 3.0 mm deep and about 1.5 to 3.5 mm across; limb bent outwardly in distal 16.0 mm to nearly a ninety degree angle; claw tapering to truncate base about 1.0 mm across; petals persistent.

*Petal color*.—Petal main limb abaxial between RHS 73A and N74D, adaxial main limb nearest RHS 71D; abaxial and adaxial limb base white, lighter than RHS 155D; petal claw abaxial and adaxial nearest RHS 145C with 2.0 mm transition between claw and limb lighter than RHS 155D; petal limbs lightening to adaxial nearest RHS 75B and abaxial nearest RHS 75D.

*Petal dimension*.—Size to about 37.0 mm long and about 21.0 mm across at widest part of limb, average about 36.0 mm long and about 19.0 mm wide; claw portion average about 18.0 mm long and about 1.0 mm at base; limb portion average about 22.0 mm long and 20.0 mm wide.

*Calyx*.—Glabrous, glaucous; margins entire; consisting of five sepals with acute apex and fused base forming five-toothed corolla tube fused in proximal 13.0 mm; individual sepals about 18.0 mm long and about 5.0 mm across; campanulate to about 18.0 mm long and 9.0 mm diameter.

*Calyx color*.—Abaxial between RHS 137A and RHS 137B at apex and between RHS N138D and RHS 122C at base; adaxial nearest RHS 144A; 0.5 mm wide margins both adaxial and abaxial nearest RHS 158B.

*Peduncle*.—Glabrous, glaucous, terete, about 17.0 cm long and about 3.0 mm wide at base.

*Peduncle color*.—Nearest RHS N138C.

*Bracts*.—Two, opposite, glaucous, glabrous; sessile; margin entire, lanceolate to broadly lanceolate; acute apex; about 11.0 mm long and 5.0 mm wide.

*Bract color*.—Abaxial and adaxial nearest RHS 139A; margins of about 0.5 mm both sides nearest RHS 158B.

*Bracteoles*.—Two; glaucous, glabrous; margins entire; opposite and at 90 degrees offset from and frequently just inside bracts; broadly lanceolate to deltoid; broadly acute apex; sessile bases joined at stem; about 7.0 mm long and 6.0 mm wide.

*Bracteoles color*.—Abaxial and adaxial distally nearest RHS 139A, adaxial and abaxial basal portion between RHS 145B and RHS 145C where covered by bracts; margins transparent.

*Androecium*.—Up to twelve stamens. Filaments: typically about 23.0 m long, less than about 1.0 mm diameter; color nearest RHS 155A. Anther: elliptic-oblong, dorsifixed; about 2.0 mm long and about 1.0 mm wide; color nearest RHS 158C. Pollen: abundant; color nearest RHS 158C.

*Gynoecium*.—Style: typically split in two just above ovary. Pistil: glabrous abaxial surface and puberulent adaxial surface; irregularly curled or arched apart; about 22.0 mm long and about 1.0 mm diameter; color nearest RHS 155D. Ovary: superior; ellipsoid-shaped; about 7.0 mm long and 4.0 mm wide; color between RHS 145B and RHS 145C. Stigma: puberulent; about 1.0 cm long and 1.0 mm wide; irregularly curled; color nearest RHS 155D.

Fruit: Capsule; ovoid to cylindrical; opening by 4 teeth; about 1.8 cm long and 7.5 mm diameter; color between RHS 164B and RHS 164A when dried.

Seed: 1 to 6, blackish brown darker than RHS 200A, shield-shaped, dorsiventrally flattened, . about 3.0 mm across and 0.5 mm thick.

Disease resistance: The new plant is resistance to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct *Dianthus* plant named 'Sweetie Pie' essentially as herein described and illustrated.

* * * * *